US007381214B1

(12) United States Patent
Pruett

(10) Patent No.: US 7,381,214 B1
(45) Date of Patent: Jun. 3, 2008

(54) CONTROL SYSTEM FOR LIFT ASSEMBLY ASSOCIATED WITH CHIROPRACTIC DROP MECHANISM

(75) Inventor: Blake Pruett, Chattanooga, TN (US)

(73) Assignee: Encore Medical Asset Corporation, Henderson, NV (US)

(*) Notice: Subject to any disclaimer, the term of this patent is extended or adjusted under 35 U.S.C. 154(b) by 331 days.

(21) Appl. No.: 11/210,613

(22) Filed: Aug. 24, 2005

(51) Int. Cl.
*A61F 5/00* (2006.01)
*A47B 7/00* (2006.01)
*A47B 7/02* (2006.01)

(52) U.S. Cl. .............................. 606/237; 5/611; 5/612; 5/613

(58) Field of Classification Search ................ 606/237, 606/240-245; 128/845; 5/611-613
See application file for complete search history.

(56) References Cited

U.S. PATENT DOCUMENTS

| | | | | |
|---|---|---|---|---|
| 4,050,454 | A | | 9/1977 | Ekholm |
| 4,230,100 | A | | 10/1980 | Moon |
| 4,245,626 | A | | 1/1981 | Paolino |
| 4,314,552 | A | | 2/1982 | Moon |
| 4,445,504 | A | | 5/1984 | Barge |
| 4,523,581 | A | | 6/1985 | Ekholm |
| 4,582,311 | A | | 4/1986 | Steffensmeier |
| 4,732,141 | A | | 3/1988 | Steffensmeier |
| 4,960,111 | A | | 10/1990 | Steffensmeier |
| 4,995,378 | A | * | 2/1991 | Dyer et al. ................. 606/241 |
| 5,782,870 | A | | 7/1998 | McAfee |
| 5,794,286 | A | | 8/1998 | Scott et al. |
| 5,954,750 | A | | 9/1999 | Steffensmeier |
| 6,547,809 | B1 | | 4/2003 | Cuccia |
| 6,679,905 | B2 | | 1/2004 | Peetros et al. |
| 2002/0120293 | A1 | | 8/2002 | Peetros et al. |
| 2003/0216781 | A1 | | 11/2003 | Cuccia |

* cited by examiner

*Primary Examiner*—Justine R Yu
*Assistant Examiner*—Kristen C Matter
(74) *Attorney, Agent, or Firm*—Chambliss, Bahner & Stophel, P.C.

(57) ABSTRACT

A therapeutic treatment table includes a frame and a table section for supporting at least a portion of the body of a patient. The table section includes a body support and a drop mechanism that is mounted between the frame and the body support and adapted to drop the body support from an upper position to a lower position. A fluid actuator is mounted between the frame and the body support and adapted to raise the body support from the lower position to the upper position, and a mechanism is provided for controlling the flow of fluid to the fluid actuator in order to control the rate by which the fluid actuator raises the body support from the lower position to the upper position.

8 Claims, 5 Drawing Sheets

CONTROL SYSTEM FOR LIFT ASSEMBLY ASSOCIATED WITH CHIROPRACTIC DROP MECHANISM

FIELD OF THE INVENTION

The present invention relates generally to medical rehabilitation devices, and more particularly to a therapeutic treatment table which includes a table section that is adapted to move abruptly and rapidly through a controlled distance when a force or pressure is applied to a body part that is supported on the table section by a chiropractor or other therapist.

BACKGROUND OF THE INVENTION

Chiropractic tables are known for use in treating patients suffering from a variety of orthopedic and neuropathic maladies. Such treatments include placing the patient's spine in vertical flexion (head to chest motion), extension (head to back motion), lateral flexion (left and right motion) and rotation (turning motion), as well as coupling vertical and lateral flexion to produce circumduction. Chiropractic tables are described in U.S. Pat. No. 4,050,454 of Ekholm, U.S. Pat. No. 4,230,100 of Moon, U.S. Pat. No. 4,245,626 of Paolino, U.S. Pat. No. 4,314,552 of Moon, U.S. Pat. No. 4,523,581 of Ekholm, U.S. Pat. No. 4,649,905 of Barnes, U.S. Pat. No. 5,794,286 of Scott et al., U.S. Pat. No. 5,954,750 of Steffensmeier and U.S. Pat. No. 6,679,905 of Peetros, et al. Chiropractic tables commonly include one or more sections, some or all of which may include a drop mechanism for use in treating a particular portion of the patient's body. Generally, these drop mechanisms include an actuating mechanism that allows the table section, or a portion of the table section, to move abruptly and rapidly through a controlled distance when a force or pressure is applied to a body part that is supported on the table section by a chiropractor or other therapist. It is common for a chiropractor or other therapist to employ a series of drop treatments in succession in order to provide a therapeutic benefit. Consequently, a mechanism must be provided to raise the drop section of the table back up to its "pre-drop" level after each drop treatment. Some chiropractic tables are provided with a manually-operated "cocking" device to raise the drop section by using a hand lever to rotate a cocking shaft that is connected to the drop section. However, a disadvantage of such mechanisms is that they are time-consuming to operate and require considerable effort on the part of the practitioner, particularly if the patient is heavy. Other tables include a cocking device which includes a fluid actuator that is employed to raise the drop section. However, these actuators tend to raise the drop section rather quickly, and some patients find this uncomfortable and/or disconcerting. U.S. Pat. No. 4,245,626 of Paolino describes a table which includes a motorized cocking device in which an electric motor, a speed reducing gear train and an eccentric linkage assembly are employed to rotate a cocking shaft to raise the drop section. Although this motorized cocking device is reported to provide a "gentle cocking action which will not injure or alarm the patient", it does require a complicated and expensive assembly of components.

It would be desirable, therefore, if a therapeutic device could be developed for providing a controlled cocking action to raise the drop section at a rate that is comfortable for the patient. It would also be desirable if such a device could be provided utilizing reliable and inexpensive components.

ADVANTAGES OF THE INVENTION

Among the advantages of the invention is that it provides a therapeutic device in the form of a chiropractic table having a drop assembly which includes a cocking device that may be utilized to raise the drop section in a manner that is controlled for patient comfort. Another advantage of the invention is that it provides such a device utilizing a conventional fluid actuator for raising the drop section.

Other advantages and features of this invention will become apparent from an examination of the drawings and the ensuing description.

Explanation of Technical Terms

As used herein, the term "drop mechanism" and similar terms refer to a system or device associated with a section of a therapeutic table which includes an actuating mechanism that allows the table section, or a portion of the table section, to move abruptly and rapidly through a controlled distance. Preferably, the drop mechanism is actuated when an external force is applied to the table section or to a body part that is supported on the table section.

As used herein, the term "drop section" and similar terms refer to a section of a therapeutic table that includes a drop mechanism.

As used herein, the term "drop treatment" and similar terms refer to a treatment of a patient supported on a therapeutic table having a drop section in which an external force is applied to the drop section or to a body part that is supported on the drop section to engage an actuating mechanism that allows the drop section or a portion thereof to move abruptly and rapidly through a controlled distance.

As used herein, the term "cocking" and similar terms refer to the action of raising a drop section of a table and placing it in position to initiate a drop treatment.

As used herein, the term "cocking device" and similar terms refer to a device or assembly that is employed to raise a drop section of a table and to place it in position to initiate a drop treatment.

As used herein, the term "fluid actuator" and similar terms refers to a pneumatic or hydraulic device which includes a cylinder, a piston within the cylinder, and a rod attached to the piston. Fluid pressure within the cylinder on one side of the piston (over that on the opposite side of the piston) will cause the rod to extend from the cylinder or to retract into the cylinder.

As used herein, the term "drop assembly" and similar terms refer to an assembly that includes a drop mechanism and a cocking device.

SUMMARY OF THE INVENTION

The invention comprises a therapeutic treatment table having a frame and a table section for supporting at least a portion of the body of a patient. The table section includes a body support and a drop mechanism that is mounted between the frame and the body support and adapted to drop the body support from an upper position to a lower position. The table section also includes a fluid actuator that is mounted between the frame and the body support and adapted to raise the body support from the lower position to the upper position. The therapeutic treatment table also includes means for controlling the flow of fluid to the fluid actuator in order to control the rate by which the fluid actuator raises the body support from the lower position to the upper position. A preferred embodiment of the invention includes a fluid circuit connecting a source of fluid and the fluid actuator, and a variable flow valve in the fluid circuit for controlling the amount of fluid to the fluid actuator.

In order to facilitate an understanding of the invention, the preferred embodiments of the invention are illustrated in the drawings, and a detailed description thereof follows. It is not intended, however, that the invention be limited to the particular embodiments described or to use in connection with the apparatus illustrated herein. Various modifications and alternative embodiments such as would ordinarily occur to one skilled in the art to which the invention relates are also contemplated and included within the scope of the invention described and claimed herein.

BRIEF DESCRIPTION OF THE DRAWINGS

The presently preferred embodiments of the invention are illustrated in the accompanying drawings, in which.

DESCRIPTION OF THE PREFERRED EMBODIMENTS OF THE INVENTION

Figure 1:
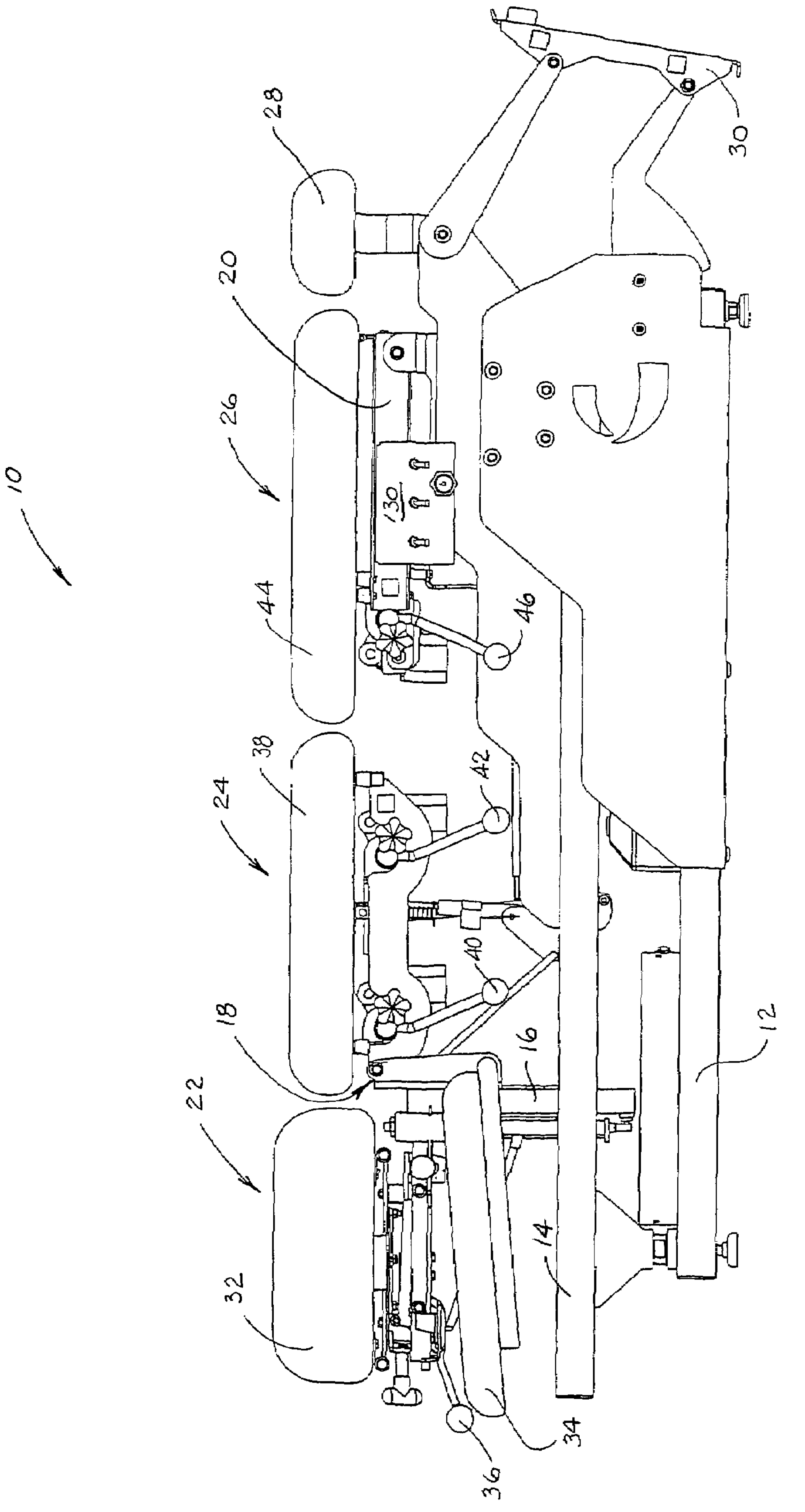
FIG. 1 is a side view of a preferred embodiment of a therapeutic treatment table which includes or comprises the invention.

Referring now to the drawings, FIG. 1 illustrates a preferred embodiment of a chiropractic table or therapeutic treatment table 10 having a frame comprised of base 12 and several frame components, including components 14, 16, 18 and 20. Table 10 also includes three table sections that are adapted to move with respect to the frame in providing a therapeutic treatment to a patient. These sections are head section 22, thoracic/lumbar section 24 and pelvic section 26. Head section 22 is adapted to support the head of a patient, thoracic/lumbar section 24 is adapted to support the chest of a patient, and pelvic section 26 is adapted to support the patient's pelvis and a portion of his legs. Table 10 also includes ankle support 28 and foot plate 30. In the illustrated embodiment of the invention, table 10 is adapted to be pivoted so as to raise the table to a nearly vertical attitude with the head section at the top and the foot plate being pivoted to lie flat on the floor (although such position is not shown in the drawings). In such position, a patient who is unable to easily lie down on a horizontal table can be accommodated, and the pivoting mechanism of the table employed to bring the table (with the patient thereon) to a horizontal attitude.

It is common that the patient be placed face down on the table with his head supported by a body support comprising a pair of head cushions 31 (shown in FIG. 5) and 32 that are slightly spaced apart. A pair of arm cushions 33 (shown in FIG. 5) and 34 are also provided. Head section 22 also includes a cervical drop mechanism, which is mounted between the frame and the body support and adapted to drop the body support abruptly and rapidly through a controlled distance from the upper position shown in FIG. 1 to a lower position (not shown) which is typically a few inches directly below the upper position. Preferably, the drop mechanism is actuated when an external force is applied to the table section or to a body part that is supported on the table section by a chiropractor or other therapist. Forward drop cocking lever 36 may be used to place head section 22, which has been raised to its upper position, in condition for a drop treatment.

Thoracic/lumbar section 24 includes a body support comprising thoracic/lumbar cushion 38, and a pair of drop mechanisms, which are mounted between the frame and the body support. Each of the drop mechanisms is adapted to drop an end of the body support abruptly and rapidly through a controlled distance from the upper position shown in FIG. 1 to a lower position (not shown) which is typically a few inches below the upper position, while the other end of the table section pivots about a generally horizontal axis (not shown), so that section 24 tilts downwardly during a drop treatment. Preferably, the drop mechanism is actuated when an external force is applied to the table section or to a body part that is supported on the table section by a chiropractor or other therapist. Thoracic drop cocking lever 40 may be used to place the forward portion of thoracic/lumbar section 24 (i.e. that portion nearest head section 22), which has been raised to its upper position (as shown in FIG. 1), in condition for a drop treatment. Similarly, lumbar drop cocking lever 42 may be used to place the rear portion of thoracic/lumbar section 24 (i.e. that portion nearest pelvic section 26), which has been raised to its upper position (as shown in FIG. 1), in condition for a drop treatment.

Pelvic section 26 includes a body support comprising pelvic cushion 44, and a pelvic drop mechanism, which is mounted between the frame and the body support and adapted to drop the body support abruptly and rapidly through a controlled distance from the upper position shown in FIG. 1 to a lower position (not shown) which is typically a few inches directly below the upper position. Preferably, the drop mechanism is actuated when an external force is applied to the table section or to a body part that is supported on the table section by a chiropractor or other therapist. Pelvic drop cocking lever 46 may be used to place the pelvic section, which has been raised to its upper position (as shown in FIG. 1), in condition for a drop treatment.

Although the preferred embodiment of the invention includes a head section with a single drop mechanism, a thoracic/lumbar section with a pair of drop mechanisms and a pelvic section with a single drop mechanism, any of the three table sections may include one or more drop mechanisms, as is known to those having ordinary skill in the art to which the invention relates. Furthermore, in the preferred embodiment of the invention that is illustrated in the drawings, each drop mechanism comprises a part of a drop assembly which includes a cocking device that is employed to raise the drop section from its lower position to its upper position and to place it in position to initiate a drop treatment.

Figure 2:
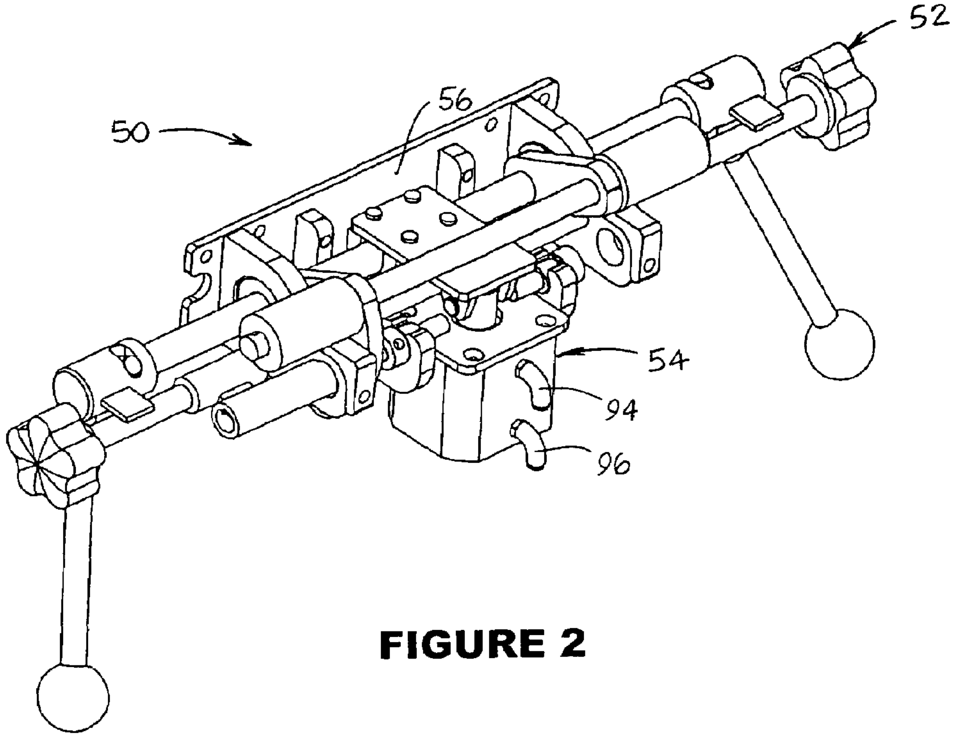
FIG. 2 is a perspective view of a preferred drop assembly that is employed in the therapeutic treatment table of FIG. 1.
Figure 3:
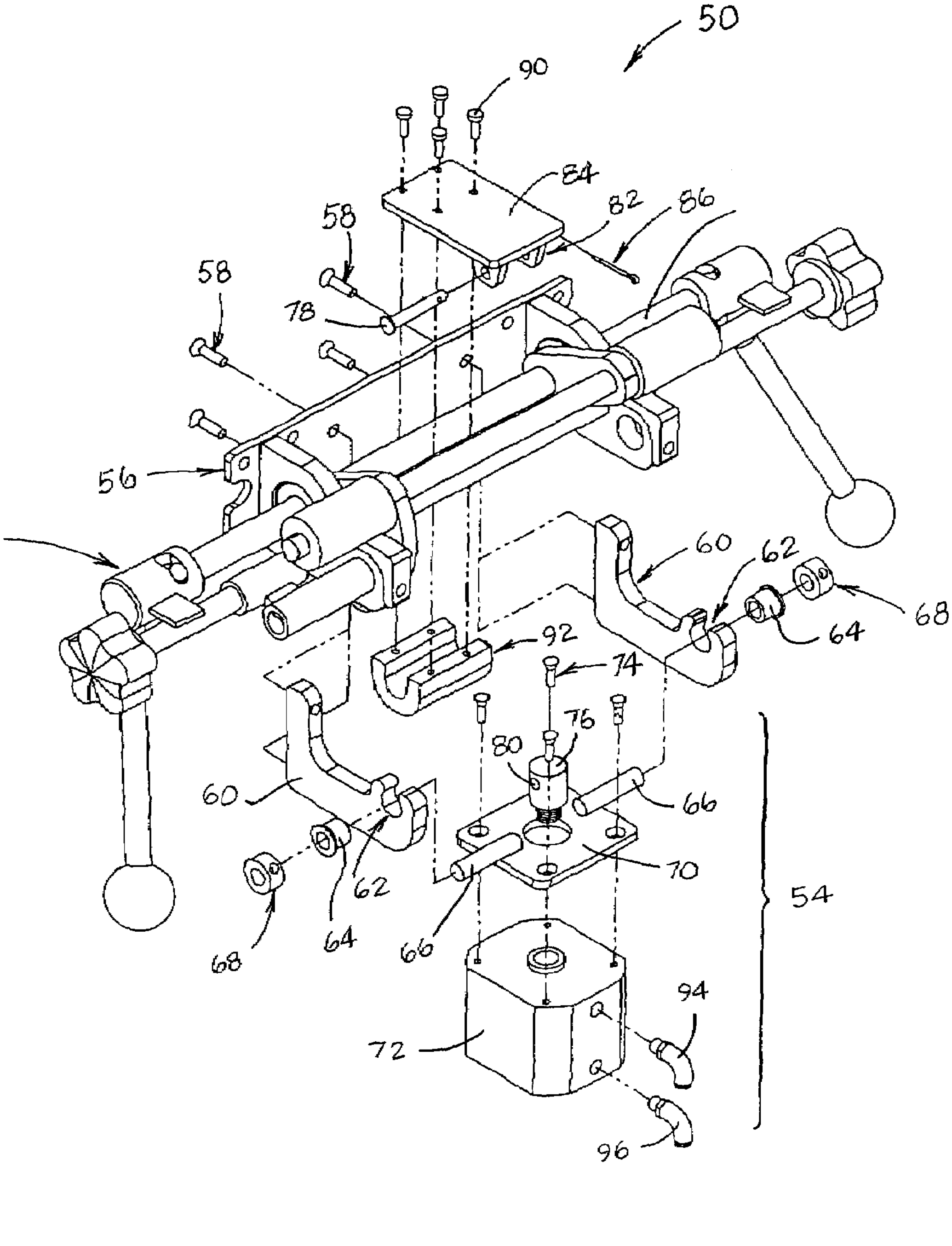
FIG. 3 is an exploded view of the assembly of FIG. 2.

Referring now to FIGS. 2 and 3, pelvic drop assembly 50, which is exemplary of all of the drop assemblies of a preferred embodiment of the invention, is shown in some detail. Drop assembly 50 includes a conventional drop mechanism 52 and a fluid actuator 54. Drop mechanism includes mounting plate 56, by which the drop mechanism is mounted by conventional means to the body support of the table section. Mounted to mounting plate 56 by fasteners 58 are a pair of support arms 60. Each support arm has a slot 62 which is adapted to receive bushing 64, into which is placed pivot rod 66, which is secured therein by end fastener 68. Top plate 70 of fluid actuator 54 is attached to actuator body 72 by fasteners 74. Actuator 54 includes a rod having a cap 76 that may be raised or lowered, with respect to actuator body 72 and top plate 70, depending on the pressure differential on either side of a piston (not shown) on the rod within actuator body 72. Pin 78 extends through hole 80 in rod cap 76 and through holes in bracket 82 of upper plate 84, and is secured by cotter pin 86. Upper plate 84 is mounted over rod 88 of the drop mechanism by fasteners 90, which extend into suitable holes in lower mount 92. The upper plate is also attached (not shown) to a lower part of the body support. Preferred fluid actuator 54 is a double acting pneumatic actuator that is attached (not shown) to a frame component. Fluid actuator 54 includes rod end port 94 and cap end port 96, through which air may be selectively directed to raise or lower the rod with respect to the actuator body. In raising the rod with respect to the actuator body, the fluid actuator serves to raise the body support with respect to the frame of the therapeutic treatment table.

Figure 4:
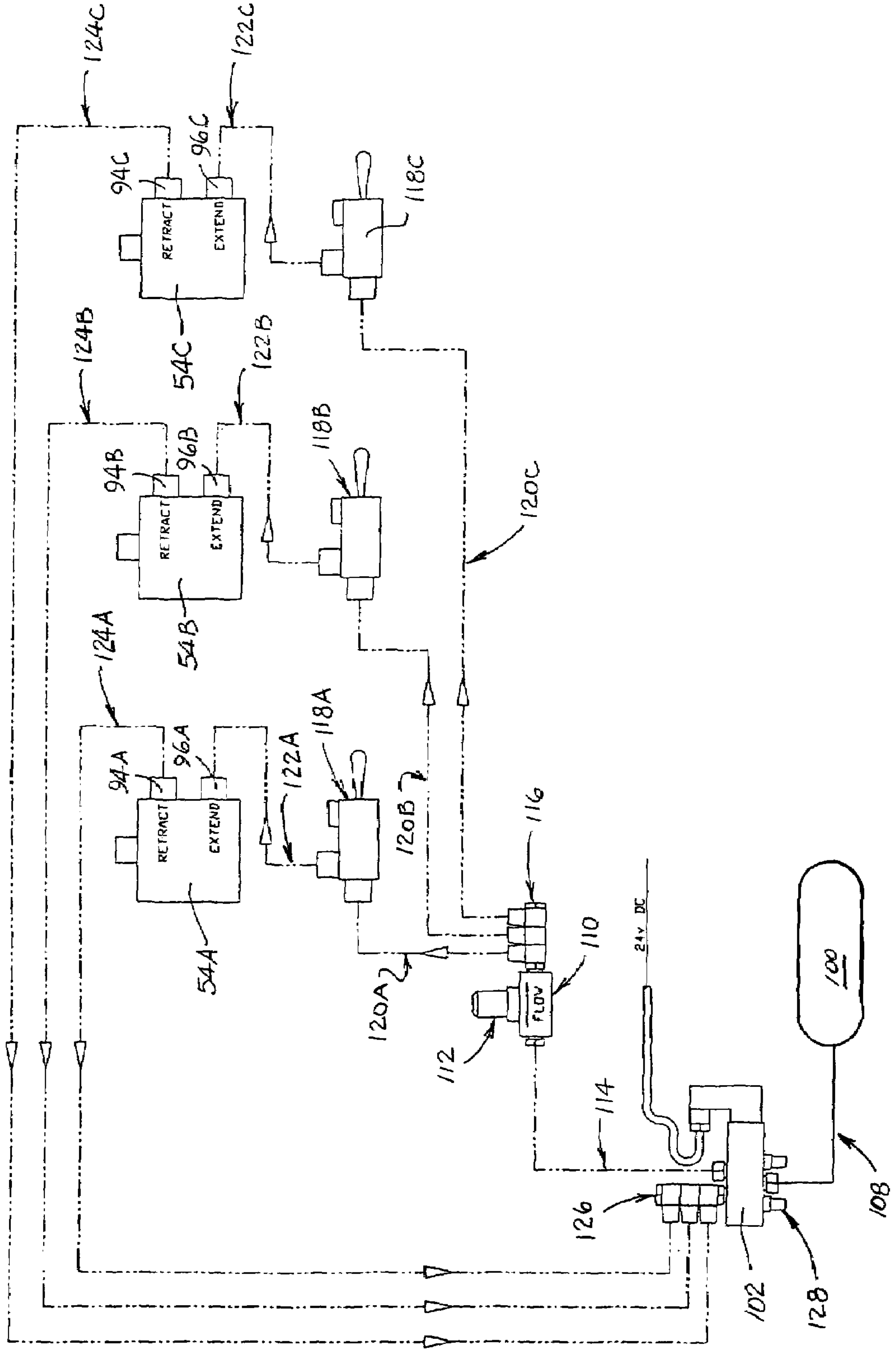
FIG. 4 is a schematic illustration of the fluid circuit of a preferred embodiment of the invention.
Figure 5:
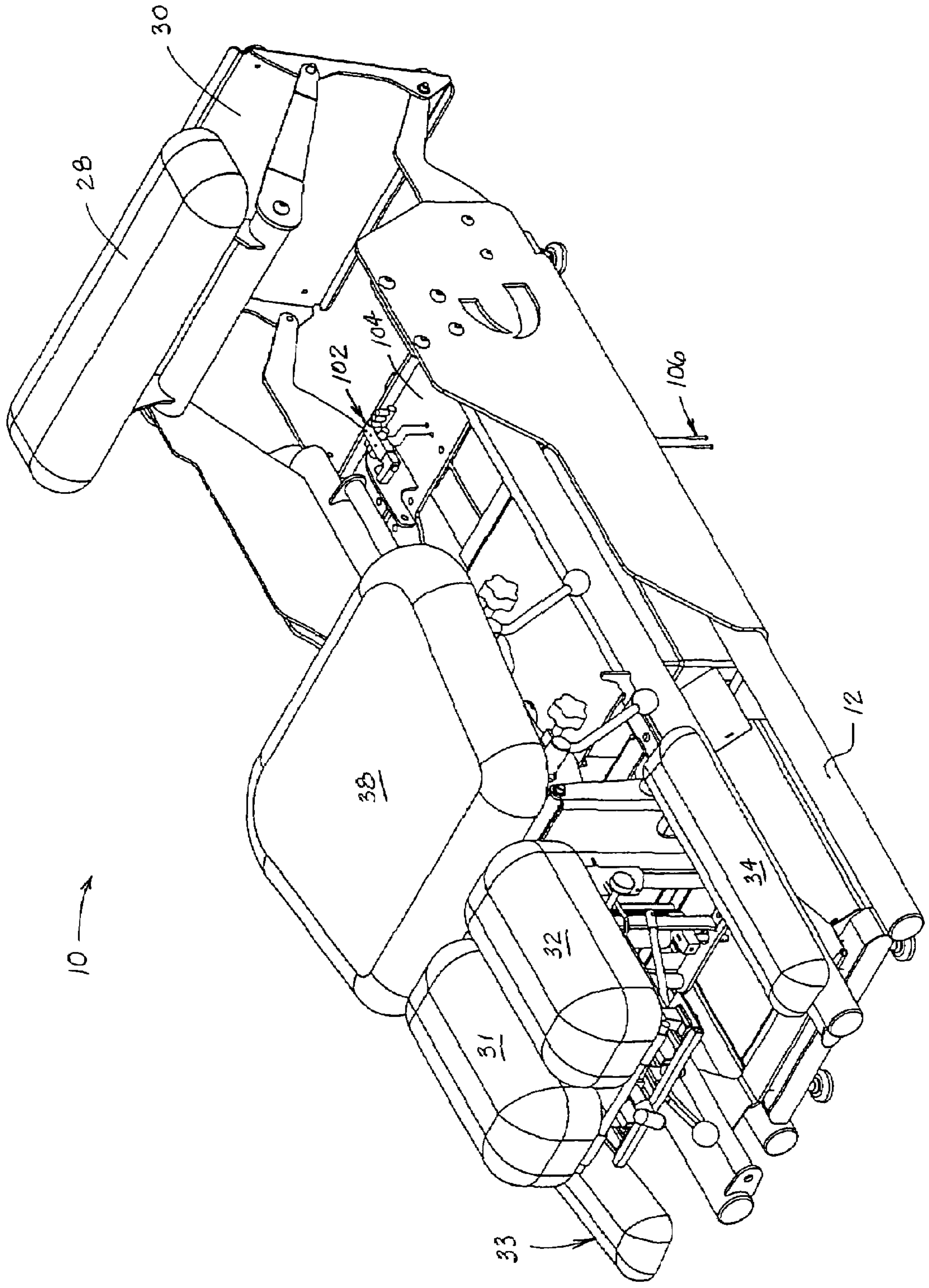
FIG. 5 is a perspective view of the therapeutic treatment table of FIG. 1 with the pelvic section removed to show the location of an on/off valve that is employed in connection with a preferred embodiment of the invention.

The invention includes means for controlling the flow of fluid to a fluid actuator in order to control the rate by which such fluid actuator raises the body support with which it is associated from the lower position to the upper position. Referring now to FIG. 4, the preferred means for controlling the flow of fluid to a fluid actuator comprises a source of fluid, indicated schematically at 100, and a fluid circuit connecting the source of fluid and the fluid actuator. Three such actuators, fluid actuators 54A, 54B and 54C are illustrated in FIG. 4, although any convenient number of actuators may be connected by the fluid circuit of a preferred embodiment of the invention. An on/off valve, preferably solenoid valve 102, is connected by suitable circuitry to a source of electric power (not shown). FIG. 5 shows the preferred location for on/off valve 102. As shown therein, valve 102 is attached to base plate 104 of table 10 by fasteners 106.

Referring again to FIG. 4, first fluid supply line 108 connects fluid source 100 and the input side of on/off valve 102. Variable flow valve 110 is provided to control the flow of fluid to each fluid actuator, and preferably comprises a variable opening needle valve which is controlled by knob 112. Second fluid supply line 114 connects the output side of on/off valve 102 and the input side of variable flow valve 110. Since the illustrated embodiment includes three fluid actuators, a triple elbow fitting 116 is attached to the output side of variable flow valve 110. A switch valve is associated with each fluid actuator and is adapted to open and close the portion of the fluid circuit to the fluid actuator with which it is associated. As shown in FIG. 4, switch valve 118A is associated with fluid actuator 54A, switch valve 118B is associated with fluid actuator 54B, and switch valve 118C is associated with fluid actuator 54C. A switch fluid supply line connects the variable flow valve to each switch valve. Thus, switch fluid supply line 120A is connected to the output side of variable flow valve 110 (through elbow fitting 116) and to the input side of switch valve 118A. Similarly, switch fluid supply line 120B is connected to the output side of variable flow valve 110 and to the input side of switch valve 118B, and switch fluid supply line 120C is connected to the output side of variable flow valve 110 and to the input side of switch valve 118C. An actuator supply line connects the output side of each switch valve to the cap end port of the fluid actuator associated therewith. Thus, actuator supply line 122A connects the output side of switch valve 118A to cap end port 96A of fluid actuator 54A, actuator supply line 122B connects the output side of switch valve 118B to cap end port 96B of fluid actuator 54B, and actuator supply line 122C connects the output side of switch valve 118C to cap end port 96C of fluid actuator 54C. Finally, a retraction line connects the rod end port of each fluid actuator to the retraction side of on/off valve 102 through triple elbow fitting 128, so that on/off valve may also be employed to retract the rod of the fluid actuator after the table section has been placed in position for a drop treatment. Thus, retraction line 124A connects rod end port 94A of fluid actuator 54A to on/off valve 102 through triple elbow fitting 128, retraction line 124B connects rod end port 94B of fluid actuator 54B to on/off valve 102, and retraction line 124C connects rod end port 94C of fluid actuator 54C to on/off valve 102. Retraction port 128 is provided on valve 102 to provide for connection of a fluid supply such as supply 100 in order to initiate retraction of the rods of the fluid actuators.

Figure 6:
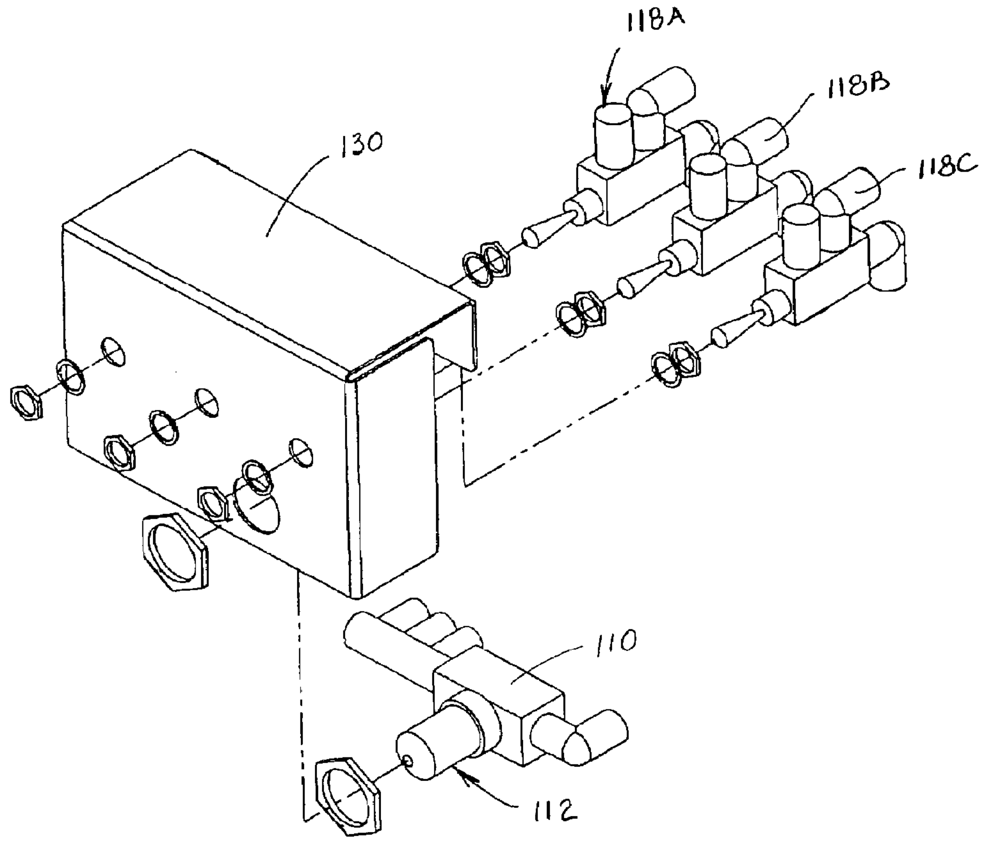
FIG. 6 is an exploded perspective view of the control assembly of a preferred embodiment of the invention.

Referring now to FIGS. 1 and 6, the preferred location for variable flow valve 110 and switch valves is shown. As shown in FIG. 6, valve 110 and valves 118A, 118B and 118C are preferably mounted in control box 130 which is mounted onto the side of table 10 (as shown in FIG. 1). In operating the preferred embodiment of the invention, on/off valve 102 admits air or another fluid to variable flow valve 110. By adjusting the opening of valve 110, an operator can control the amount of air (or another fluid) which is directed to switches 118. One each of switches 118 is preferably provided for the fluid actuator of the thoracic drop cocking device, the fluid actuator of the lumbar drop cocking device and the fluid actuator of the pelvic drop cocking device. Each of switches 118 may be set either "on" or "off", depending on whether the operator desires to extend the rod of the fluid actuator associated therewith to raise the body support of that section of the table. Obviously, if valve 110 is wide open, there will be no restriction to the flow of fluid through an open switch 118 to a fluid actuator, and the rod of the actuator will rise rather quickly. The more the opening through valve 110 is restricted, the lower the rate of flow of fluid through an open switch, and the lower the speed of rise of the associated body support of that section of the table.

Although this description contains many specifics, these should not be construed as limiting the scope of the invention but as merely providing illustrations of some of the presently preferred embodiments thereof, as well as the best mode contemplated by the inventor of carrying out the invention. The invention, as described herein, is susceptible to various modifications and adaptations, and the same are intended to be comprehended within the meaning and range of equivalents of the appended claims.

What is claimed is:

1. A therapeutic treatment table comprising:

(a) a frame;

(b) a table section for supporting at least a portion of the body of a patient, said table section comprising:

(i) a body support;

(ii) a drop mechanism that is mounted between the frame and the body support and adapted to drop the body support from an upper position to a lower position;

(iii) a fluid actuator that is mounted between the frame and the body support and adapted to raise the body support from the lower position to the upper position;

(c) means for controlling the flow of fluid to the fluid actuator in order to control the rate by which the fluid actuator raises the body support from the lower position to the upper position, said means comprising:

(i) a source of fluid;

(ii) a fluid circuit connecting the source of fluid and the fluid actuator, said fluid circuit comprising:

(A) a variable flow valve;

(B) an on/off valve;

(C) a first fluid supply line connecting the source of fluid and the on/off valve;

(D) a second fluid supply line connecting the on/off valve and the variable flow valve;

(E) a switch valve that is associated with the fluid actuator;

(F) a switch fluid supply line which connects the variable flow valve and the switch valve;

said fluid circuit being adapted for controlling the amount of fluid to the fluid actuator in order to control the rate by which said fluid actuator raises the body support from the lower position to the upper position.

2. The therapeutic treatment table of claim 1 wherein the variable flow valve comprises a variable opening needle valve.

3. The therapeutic treatment table of claim 1 wherein the on/off valve comprises a solenoid valve.

4. A therapeutic treatment table comprising:

(a) a frame;

(b) a plurality of table sections for supporting at least a portion of the body of a patient, wherein each such table section comprises:

(i) a body support;

(ii) a drop mechanism that is mounted between the frame and the body support and adapted to drop the body support from an upper position to a lower position;

(iii) a fluid actuator that is mounted between the frame and the body support and adapted to raise the body support from the lower position to the upper position;

(c) a source of fluid;

(d) a fluid circuit connecting the source of fluid and each fluid actuator, said fluid circuit comprising:

(i) an on/off valve;

(ii) a first fluid supply line connecting the source of fluid and the on/off valve;

(iii) a variable flow valve;

(iv) a second fluid supply line connecting the on/off valve and the variable flow valve;

(v) a plurality of switch valves one for each fluid actuator;

(vi) a plurality of switch fluid supply lines, each of which connects the variable flow valve and a switch valve for one of the fluid actuators:

said fluid circuit being adapted for controlling the flow of fluid to each fluid actuator in order to control the rate by which each fluid actuator raises the body support with which it is associated from the lower position to the upper position.

5. The therapeutic treatment table of claim 4 wherein the variable flow valve comprises a variable opening needle valve.

6. The therapeutic treatment table of claim 4 wherein the on/off valve comprises a solenoid valve.

7. In a therapeutic treatment table having:

(a) a frame;

(b) a table section for supporting at least a portion of the body of a patient, said table section comprising:

(i) a body support;

(ii) a drop mechanism that is mounted between the frame and the body support and adapted to drop the body support from an upper position to a lower position;

the improvement which comprises:

(c) a fluid actuator that is mounted between the frame and the body support and adapted to raise the body support from the lower position to the upper position;

(d) means for controlling the flow of fluid to the fluid actuator in order to control the rate by which the fluid actuator raises the body support from the lower position to the upper position, said means comprising:

(i) a source of fluid;

(ii) a fluid circuit connecting the source of fluid and the fluid actuator, said fluid circuit comprising:

(A) a variable flow valve;

(B) an on/off valve;

(C) a first fluid supply line connecting the source of fluid and the on/off valve;

(D) a second fluid supply line connecting the on/off valve and the variable flow valve;

a switch valve that is associated with the fluid actuator;

a switch fluid supply line which connects the variable flow valve and the switch valve;

said fluid circuit being adapted for controlling the amount of fluid to the fluid actuator in order to control the rate by which said fluid actuator raises the body support from the lower position to the upper position.

8. The improvement in the therapeutic treatment table of claim 7, wherein the variable flow valve in the fluid circuit for controlling the amount of fluid to the fluid actuator comprises a variable opening needle valve.

* * * * *